United States Patent
Moorehead et al.

(10) Patent No.: US 8,079,987 B2
(45) Date of Patent: *Dec. 20, 2011

(54) VALVED CATHETERS INCLUDING HIGH FLOW RATE CATHETERS

(75) Inventors: H. Robert Moorehead, Salt Lake City, UT (US); Brian J. Bergeron, Worcester, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 808 days.

This patent is subject to a terminal disclaimer.

(21) Appl. No.: 11/765,956

(22) Filed: Jun. 20, 2007

(65) Prior Publication Data

US 2007/0276313 A1    Nov. 29, 2007

Related U.S. Application Data

(63) Continuation of application No. 10/651,535, filed on Aug. 29, 2003, now Pat. No. 7,252,652.

(51) Int. Cl.
*A61M 5/00* (2006.01)

(52) U.S. Cl. ......... 604/247; 604/246; 604/533; 604/537

(58) Field of Classification Search .............. 604/246, 604/247, 533, 537, 264, 523, 534, 535, 905, 604/30, 31, 167.01, 167.03, 167.05, 93.01; 137/845, 493, 493.9

See application file for complete search history.

(56) References Cited

U.S. PATENT DOCUMENTS

| | | | |
|---|---|---|---|
| 2,720,881 A | 10/1955 | Weaver et al. | |
| 3,113,586 A | 12/1963 | Edmark, Jr. | |
| 3,159,175 A | 12/1964 | MacMillan | |
| 3,159,176 A | 12/1964 | Russell et al. | |
| 3,477,438 A | 11/1969 | Allen et al. | |
| 3,514,438 A | 5/1970 | Nelsen et al. | |

(Continued)

FOREIGN PATENT DOCUMENTS

DE    20208420    10/2002

(Continued)

OTHER PUBLICATIONS

Extended European Search Report; Communication; Reference No. 097EP1928 GO/NH; Application No./Patent No. 09169624.5-2310; dated Sep. 30, 2009; 6 Pages.

(Continued)

*Primary Examiner* — Kevin C Sirmons
*Assistant Examiner* — Laura Schell
(74) *Attorney, Agent, or Firm* — Bingham McCutchen LLP

(57) ABSTRACT

A pressure activated two-way slit valve assembly is designed to be used in combination with, but not limited to, a high flow rate catheter to prevent accidental ingestion of air or loss of blood if the closure cap comes off during non-use of the catheter. In addition, the potential for occlusion of the catheter due to blood clots in the catheter and catheter related infection is substantially reduced. The pressure activated two-way slit valve assembly includes a first end, a second end, a wall defining a dumbbell shaped channel, and a flexible, thin disk having a slit and positioned within the pressure activated two-way slit valve assembly to reside within the dumbbell shaped channel. The slit and the dumbbell shaped channel are sized to enable the slit to deform in response to a predetermined pressure differential across the slit to allow fluid to pass therethrough.

27 Claims, 8 Drawing Sheets

U.S. PATENT DOCUMENTS

| | | |
|---|---|---|
| 3,525,357 A | 8/1970 | Koreski |
| 3,621,557 A | 11/1971 | Cushman et al. |
| 3,669,323 A | 6/1972 | Harker et al. |
| 3,673,612 A | 7/1972 | Merrill et al. |
| 3,674,183 A | 7/1972 | Venable et al. |
| 3,811,466 A | 5/1974 | Ohringer |
| 3,955,594 A | 5/1976 | Snow |
| 4,072,146 A | 2/1978 | Howes |
| 4,142,525 A | 3/1979 | Binard et al. |
| 4,143,853 A | 3/1979 | Abramson |
| 4,405,316 A | 9/1983 | Mittleman |
| 4,434,810 A | 3/1984 | Atkinson |
| 4,447,237 A | 5/1984 | Frisch et al. |
| 4,468,224 A | 8/1984 | Enzmann et al. |
| 4,543,087 A | 9/1985 | Sommercorn et al. |
| 4,552,553 A | 11/1985 | Schulte et al. |
| 4,610,665 A | 9/1986 | Matsumoto et al. |
| 4,616,768 A | 10/1986 | Flier |
| 4,673,393 A | 6/1987 | Suzuki et al. |
| 4,681,572 A | 7/1987 | Tokarz et al. |
| 4,692,146 A | 9/1987 | Hilger |
| 4,790,832 A | 12/1988 | Lopez |
| 4,798,594 A | 1/1989 | Hillstead |
| 4,801,297 A | 1/1989 | Mueller |
| 4,944,726 A | 7/1990 | Hilal et al. |
| 4,946,448 A | 8/1990 | Richmond |
| 5,000,745 A | 3/1991 | Guest et al. |
| 5,009,391 A | 4/1991 | Steigerwald |
| 5,030,210 A | 7/1991 | Alchas et al. |
| 5,084,015 A | 1/1992 | Moriuchi |
| 5,098,405 A | 3/1992 | Peterson et al. |
| 5,125,893 A | 6/1992 | Dryden |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,201,722 A | 4/1993 | Moorehead et al. |
| 5,205,834 A | 4/1993 | Moorehead et al. |
| 5,249,598 A | 10/1993 | Schmidt |
| 5,254,086 A | 10/1993 | Palmer et al. |
| 5,330,424 A | 7/1994 | Palmer et al. |
| 5,336,203 A | 8/1994 | Goldhardt et al. |
| 5,360,407 A | 11/1994 | Leonard et al. |
| 5,370,624 A | 12/1994 | Edwards et al. |
| 5,396,925 A * | 3/1995 | Poli .................. 137/493 |
| 5,399,168 A | 3/1995 | Wadsworth et al. |
| 5,401,255 A | 3/1995 | Sutherland et al. |
| D357,735 S | 4/1995 | McPhee |
| 5,405,340 A | 4/1995 | Fageol et al. |
| 5,411,491 A | 5/1995 | Goldhardt et al. |
| 5,453,097 A | 9/1995 | Paradis |
| 5,454,784 A | 10/1995 | Atkinson et al. |
| 5,469,805 A | 11/1995 | Gibbs et al. |
| 5,470,305 A | 11/1995 | Arnett et al. |
| 5,484,420 A | 1/1996 | Russo |
| 5,542,923 A | 8/1996 | Ensminger et al. |
| 5,554,136 A | 9/1996 | Luther |
| 5,562,618 A | 10/1996 | Cai et al. |
| 5,571,093 A | 11/1996 | Cruz et al. |
| 5,575,769 A | 11/1996 | Vaillancourt et al. |
| 5,624,395 A | 4/1997 | Mikhail et al. |
| 5,637,099 A | 6/1997 | Durdin et al. |
| 5,667,500 A | 9/1997 | Palmer et al. |
| 5,707,357 A | 1/1998 | Mikhail et al. |
| 5,743,873 A | 4/1998 | Cai et al. |
| 5,743,884 A | 4/1998 | Hasson et al. |
| 5,743,894 A | 4/1998 | Swisher |
| 5,752,938 A | 5/1998 | Flatland et al. |
| 5,803,078 A * | 9/1998 | Brauner .................. 128/207.14 |
| 5,807,349 A | 9/1998 | Person et al. |
| 5,843,044 A | 12/1998 | Moorehead |
| 5,853,397 A | 12/1998 | Shemesh et al. |
| 5,865,308 A | 2/1999 | Qin et al. |
| 5,944,698 A | 8/1999 | Fischer et al. |
| 5,984,902 A | 11/1999 | Moorehead |
| 6,033,393 A | 3/2000 | Balbierz et al. |
| 6,045,734 A | 4/2000 | Luther et al. |
| 6,050,934 A | 4/2000 | Mikhail et al. |
| 6,056,717 A | 5/2000 | Finch et al. |
| 6,062,244 A | 5/2000 | Arkans |
| 6,092,551 A | 7/2000 | Bennett |
| 6,120,483 A | 9/2000 | Davey et al. |
| 6,152,909 A | 11/2000 | Bagaoisan et al. |
| 6,210,366 B1 | 4/2001 | Sanfilippo |
| 6,227,200 B1 | 5/2001 | Crump et al. |
| 6,270,489 B1 | 8/2001 | Wise et al. |
| 6,306,124 B1 | 10/2001 | Jones et al. |
| 6,364,861 B1 | 4/2002 | Feith et al. |
| 6,364,867 B2 | 4/2002 | Wise et al. |
| 6,375,637 B1 | 4/2002 | Campbell et al. |
| 6,436,077 B1 | 8/2002 | Davey et al. |
| 6,442,415 B1 | 8/2002 | Bis et al. |
| 6,446,671 B2 | 9/2002 | Armenia et al. |
| 6,508,791 B1 | 1/2003 | Guerrero |
| 6,551,270 B1 | 4/2003 | Bimbo et al. |
| 6,610,031 B1 | 8/2003 | Chin |
| 6,726,063 B2 | 4/2004 | Stull et al. |
| 6,786,884 B1 | 9/2004 | DeCant et al. |
| 6,874,999 B2 | 4/2005 | Dai et al. |
| 6,953,450 B2 | 10/2005 | Baldwin et al. |
| 6,994,314 B2 | 2/2006 | Garnier et al. |
| 7,081,106 B1 | 7/2006 | Guo et al. |
| 7,252,652 B2 | 8/2007 | Moorehead et al. |
| 7,291,133 B1 | 11/2007 | Kindler et al. |
| 7,316,655 B2 | 1/2008 | Garibotto et al. |
| 7,435,236 B2 | 10/2008 | Weaver et al. |
| 7,601,141 B2 * | 10/2009 | Dikeman et al. ............... 604/246 |
| 7,637,893 B2 | 12/2009 | Christensen et al. |
| 7,758,541 B2 | 7/2010 | Wallace et al. |
| 2001/0023333 A1 | 9/2001 | Wisse et al. |
| 2001/0037079 A1 | 11/2001 | Burbank et al. |
| 2002/0016584 A1 | 2/2002 | Wise et al. |
| 2002/0121530 A1 | 9/2002 | Socier |
| 2002/0165492 A1 | 11/2002 | Davey et al. |
| 2002/0193752 A1 | 12/2002 | Lynn |
| 2003/0122095 A1 | 7/2003 | Wilson et al. |
| 2004/0034324 A1 | 2/2004 | Seese et al. |
| 2004/0064128 A1 | 4/2004 | Raijman et al. |
| 2004/0186444 A1* | 9/2004 | Daly et al. .................... 604/247 |
| 2004/0193119 A1* | 9/2004 | Canaud et al. ................ 604/247 |
| 2004/0267185 A1 | 12/2004 | Weaver et al. |
| 2005/0010176 A1 | 1/2005 | Dikeman et al. |
| 2005/0027261 A1 | 2/2005 | Weaver et al. |
| 2005/0043703 A1 | 2/2005 | Nordgren |
| 2005/0049555 A1 | 3/2005 | Moorehead et al. |
| 2005/0149116 A1 | 7/2005 | Edwards et al. |
| 2005/0171490 A1 | 8/2005 | Weaver et al. |
| 2005/0171510 A1 | 8/2005 | DiCarlo et al. |
| 2005/0283122 A1 | 12/2005 | Nordgren |
| 2006/0129092 A1 | 6/2006 | Hanlon et al. |
| 2006/0135949 A1 | 6/2006 | Rome et al. |
| 2006/0149211 A1 | 7/2006 | Simpson et al. |
| 2007/0161970 A1 | 7/2007 | Spohn et al. |
| 2007/0276313 A1 | 11/2007 | Moorehead et al. |
| 2008/0108956 A1 | 5/2008 | Lynn et al. |
| 2009/0292252 A1 | 11/2009 | Lareau et al. |

FOREIGN PATENT DOCUMENTS

| | | |
|---|---|---|
| EP | 0128625 | 12/1984 |
| EP | 0930082 | 7/1999 |
| EP | 1016431 | 7/2000 |
| FR | 2508008 | 12/1982 |
| FR | 2718969 | 10/1995 |
| GB | 966137 | 8/1964 |
| GB | 2102398 | 2/1983 |
| WO | WO-89/02764 | 4/1989 |
| WO | WO-92/06732 | 4/1992 |
| WO | WO-95/16480 | 6/1995 |
| WO | WO 96/17190 | 6/1996 |
| WO | WO-96/23158 | 8/1996 |
| WO | WO-96/41649 | 12/1996 |
| WO | WO-97/23255 | 7/1997 |
| WO | WO-97/26931 | 7/1997 |
| WO | WO 98/22178 | 5/1998 |
| WO | WO-99/42166 | 8/1999 |
| WO | WO-00/06230 | 2/2000 |

| WO | WO-00/44419 | 8/2000 |
| WO | WO-01/74434 | 10/2001 |
| WO | WO-03/084832 | 10/2003 |
| WO | WO-2005/023355 | 3/2005 |

OTHER PUBLICATIONS

Asch, "Venous access: options, approaches and issues," Can Assoc. Radiol J., vol. 52, No. 3 pp. 153-164 (2001).

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line,' Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

* cited by examiner

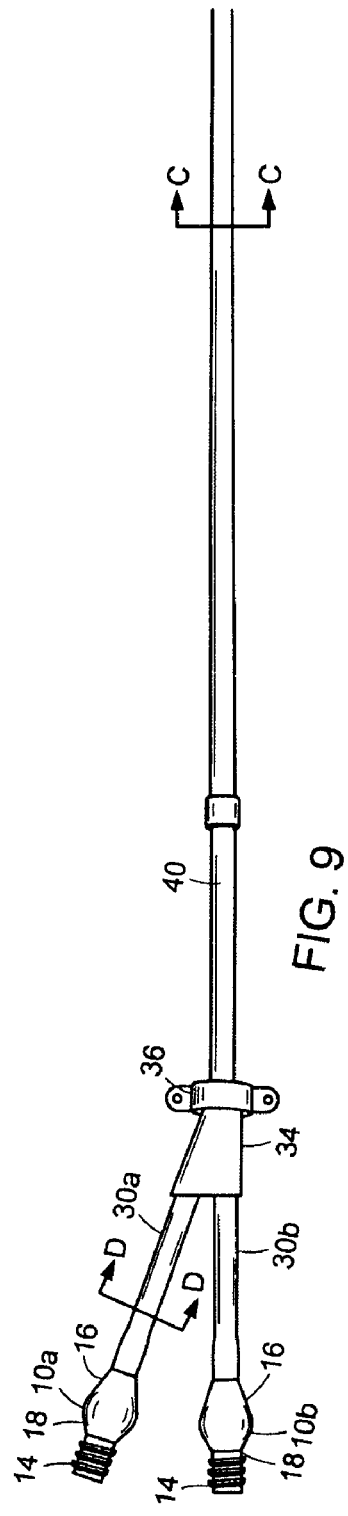
FIG. 9
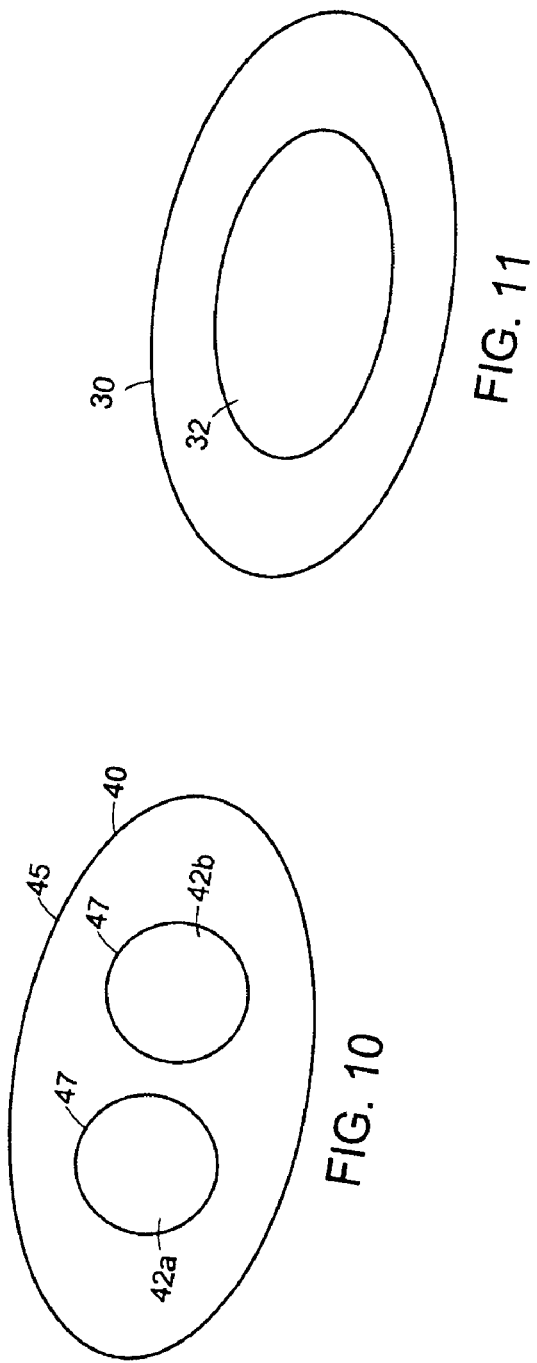
FIG. 11
FIG. 10

VALVED CATHETERS INCLUDING HIGH FLOW RATE CATHETERS

PRIORITY CLAIM

The present application is a Continuation application of U.S. patent application Ser. No. 10/651,535 filed on Aug. 29, 2003, now U.S. Pat. No. 7,252,652, Entitled "Valved Catheters Including High Flow Rate Catheters". The entire disclosure of this application is expressly incorporated herein by reference.

TECHNICAL FIELD

This invention relates to valves for catheters. More particularly, this invention relates to a valved high flow rate catheter.

BACKGROUND INFORMATION

A high flow rate catheter is a tubular medical device defining one or more lumens for transporting fluids to and/or from a patient's body at a high flow rate, e.g. greater than 200 ml/min. An example of a commonly used high flow rate catheter is a hemodialysis catheter. Hemodialysis catheters include at least one lumen for transporting a patient's waste-filled blood to a dialysis machine for treatment, and another lumen for carrying the treated blood back to the patient. Generally, hemodialysis catheters are implanted within a patient's body such that a portion remains within a blood vessel of the patient and a portion extends outside of the patient body to be connected to the dialysis machine.

Conventionally, clamps that compress the lumens of the hemodialysis catheter have been used to prevent blood loss and to preventingestion of air through the catheter and into a patient's blood stream (i.e., when the catheter is not in use). These clamps tend to degrade the hemodialysis catheter, thereby requiring medical professionals to remove and replace these catheters frequently. In addition, conventional high flow rate catheters are associated with a high occurrence of occlusion formation and infections.

SUMMARY OF THE INVENTION

The present invention generally relates to valves for catheters. While the present invention is described with regard to high flow rate catheters, it should be noted that the valves described herein may be used in combination with any type of catheter. Devices according to the invention are typically used to transport fluids to and/or from a patient's body at a high flow rate when the device is in use. It is an object of this invention to provide a device that protects against catastrophic events when the catheter is not in use, such as, for example, ingestion of air through the device into the patient's blood stream or blood flowing uncontrollably out from a patient's body. It is another object of the invention to reduce occlusion formation and infections associated with conventional high flow rate catheters.

In one aspect, the invention relates to a pressure activated two-way slit valve assembly for a catheter. The pressure activated two-way slit valve assembly includes a first end, a second end, a wall defining a dumbbell shaped channel that is locatable between the first and second ends, and a flexible, thin disk that includes a slit. The flexible, thin disk is disposed within the pressure activated two-way slit valve assembly such that the slit resides within the dumbbell shaped channel and is substantially perpendicular to a longitudinal axis of the pressure activated two-way slit valve assembly. The slit and the dumbbell shaped channel of the pressure activated two-way slit valve assembly are sized to enable the slit to deform in response to a predetermined pressure differential across the slit to allow fluid to pass therethrough.

Embodiments of this aspect of the invention can include the following features. In one embodiment, the wall of the pressure activated two-way slit valve assembly further defines connection ports that are located at the first and second ends. These connection ports are in fluid communication with the dumbbell shaped channel. In some embodiments, the first end of the pressure activated two-way slit valve assembly has a barbed ending for attaching to a catheter or other similar medical device. In another embodiment, the second end of the pressure activated two-way slit valve assembly has a luer ending for attaching to one of a dialysis machine or an end cap. In some embodiments, the flexible, thin disk has a straight slit. In other embodiments, the flexible, thin disk has an H-shaped slit. In another embodiment, the slit of the flexible, thin disk has a saw-tooth wave shape. In still yet another embodiment, the pressure activated two-way slit valve assembly includes a safety rotatable valve key that overrides the functionality of the pressure activated two-way slit valve assembly and maintains the pressure activated two-way slit valve assembly in an open position. In a further embodiment, the safety rotatable valve key is attached to the second end of the pressure activated two-way slit valve assembly.

In another aspect, the invention relates to a medical device. The medical device includes a catheter including a distal end, a proximal end, and a housing that defines one or more lumens that extend between the distal end and the proximal end. The distal end of the catheter is open whereas the proximal end is attached to a pressure activated two-way slit valve assembly comprising a first end, a second end, a wall defining a dumbbell shaped channel that is locatable between the first and second ends, and a flexible, thin disk including a slit. The flexible, thin disk is disposed within the pressure activated two-way slit valve assembly such that the slit resides within the dumbbell shaped channel and is substantially perpendicular to a longitudinal axis of the pressure activated two-way slit valve assembly. The slit and the dumbbell shaped channel are sized to enable the slit to deform in response to a predetermined pressure differential across the slit to allow fluid to pass therethrough.

Embodiments of this aspect of the invention can include the following features. In one embodiment, the wall of the pressure activated two-way slit valve assembly further defines connection ports that are located at the first and second ends of the pressure activated two-way slit valve assembly and are in fluid communication with the dumbbell shaped channel. In another embodiment, the flexible, thin disk has an H-shaped slit. Alternatively, in another embodiment, the slit of the flexible, thin disk has a saw-tooth wave shape. In some embodiments, the pressure activated two-way slit valve assembly further includes a safety rotatable valve key that overrides the functionality of the pressure activated two-way slit valve assembly and maintains the pressure activated two-way slit valve assembly in an open position. In a further embodiment, the safety rotatable valve key is attached to the second end of the pressure activated two-way slit valve assembly. In still yet another embodiment, the housing of the catheter is coated with an anti-infective coating to inhibit cell and bacteria growth.

In general, in another aspect, the invention relates to a valved dialysis catheter. The valved dialysis catheter, according to this aspect of the invention, includes an open-ended single or multi-lumen catheter including at least one lumen for withdrawing blood from a patient for dialysis and at least one lumen for returning blood from a dialysis machine to the patient. Each lumen of the open-ended multi-lumen catheter includes a pressure activated two-way slit valve assembly. Each pressure activated two-way slit valve assembly includes a first end that is connected to the open-ended single or multi-lumen catheter, a second end that is connectable to a dialysis machine, a wall extending between a first end and a second end and defining a dumbbell shaped channel that is locatable between the first and second ends, and a flexible, thin disk. The flexible thin disk includes a slit and is disposed within the pressure activated two-way slit valve assembly such that the slit resides within the dumbbell shaped channel and is substantially perpendicular to a longitudinal axis of the pressure activated two-way slit valve assembly. Both of the slit and the dumbbell shaped channel are sized to enable the slit to deform in response to a predetermined pressure differential across the slit to allow fluid to pass therethrough.

Embodiments of this aspect of the invention can include the following features. In one embodiment, the wall of the pressure activated two-way slit valve assembly further defines connection ports that are located at the first and second ends of the pressure activated two-way slit valve assembly. These connection ports are in fluid communication with the dumbbell shaped channel. In some embodiments, the first end of the pressure activated two-way slit valve assembly has a barbed ending connecting the pressure activated two-way slit valve assembly with the multi-lumen catheter. In other embodiments, the second end of the pressure activated two-way slit valve assembly has a luer ending for attaching to one of a dialysis machine or an end cap. In another embodiment, the flexible, thin disk has an H-shaped slit. Alternatively, in a further embodiment, the slit of the flexible, thin disk has a saw-tooth wave shape. In some embodiments, the pressure activated two-way slit valve assembly includes a safety rotatable valve key that overrides the functionality of the pressure activated two-way slit valve assembly and maintains the pressure activated two-way slit valve assembly in an open position. Other embodiments feature a single or multi-lumen catheter with an anti-infective external surface and further embodiments feature a single or multi-lumen catheter with an anti-infective internal surface.

In general, in another aspect, the invention relates to a method for preventing air ingestion in a valved catheter and preventing blood loss from the valved catheter. The method, according to this aspect of the invention, includes providing the medical device including the catheter described above, and using the pressure activated two-way slit valve assembly to prevent air ingestion through the catheter and into a patient's blood stream and to prevent blood loss while the valved catheter is not in use.

Embodiments of this aspect of the invention can include the following features. In one embodiment, the predetermined pressure differential across the slit of the disk within the pressure activated two-way slit valve is between about 50 cm of water and about 120 cm of water. In an alternative embodiment, the predetermined pressure differential is between about 80 cm of water and 120 cm of water. In other embodiments, the valve is designed to open at any predetermined pressure selected by a manufacturer.

The foregoing and other objects, aspects, features, and advantages of the invention will become more apparent from the following description and the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 9 is a schematic view of one embodiment of a medical device that includes a catheter and two pressure activated two-way slit valve assemblies.

FIG. 10 is a cross-sectional view of a portion of the catheter, taken along line CC of FIG. 9.

FIG. 11 is a cross-sectional view of a portion of a tubular element extending off from the catheter, taken along DD of FIG. 9.

DESCRIPTION

The kidneys are a pair of organs located near the backbone that filter and remove waste products from a human being's blood. Patients who suffer from kidney failure must undergo hemodialysis, a process in which waste products from the patient's blood are removed through passing their blood through a dialysis machine. Generally, these patients require dialysis treatments once every three days.

Hemodialysis catheters, which are a type of high flow rate catheter, are used to transport such a patient's blood to and from the dialysis machine for treatment. Typically, a portion of the hemodialysis catheter is implanted within a patient's body while a reminder of the hemodialysis catheter extends out from the body and is easily attached to the dialysis machine.

Other uses for high flow rate catheters can include rapid infusion of blood and blood products to a patient and infusion of saline to a dehydrated patient.

Some of the biggest complaints with conventional high flow rate catheters are occlusions, thrombus, and catheter-related infections. Generally, these complications arise due to, at least in part, poor fluid flow dynamics of the catheter and/or catheter parts, including, but not limited to, valve assemblies.

The present invention concerns valve assemblies for high flow rate catheters having a single lumen or multiple lumens.

A valve assembly, according to the present invention, in combination with a catheter allows for efficient fluid transport to and/or from a patient's body. This invention also concerns a valve assembly for a high flow rate catheter that prevents ingestion of air from entering the high flow rate catheter and prevents blood loss when the catheter is not in use.

Figure 1:
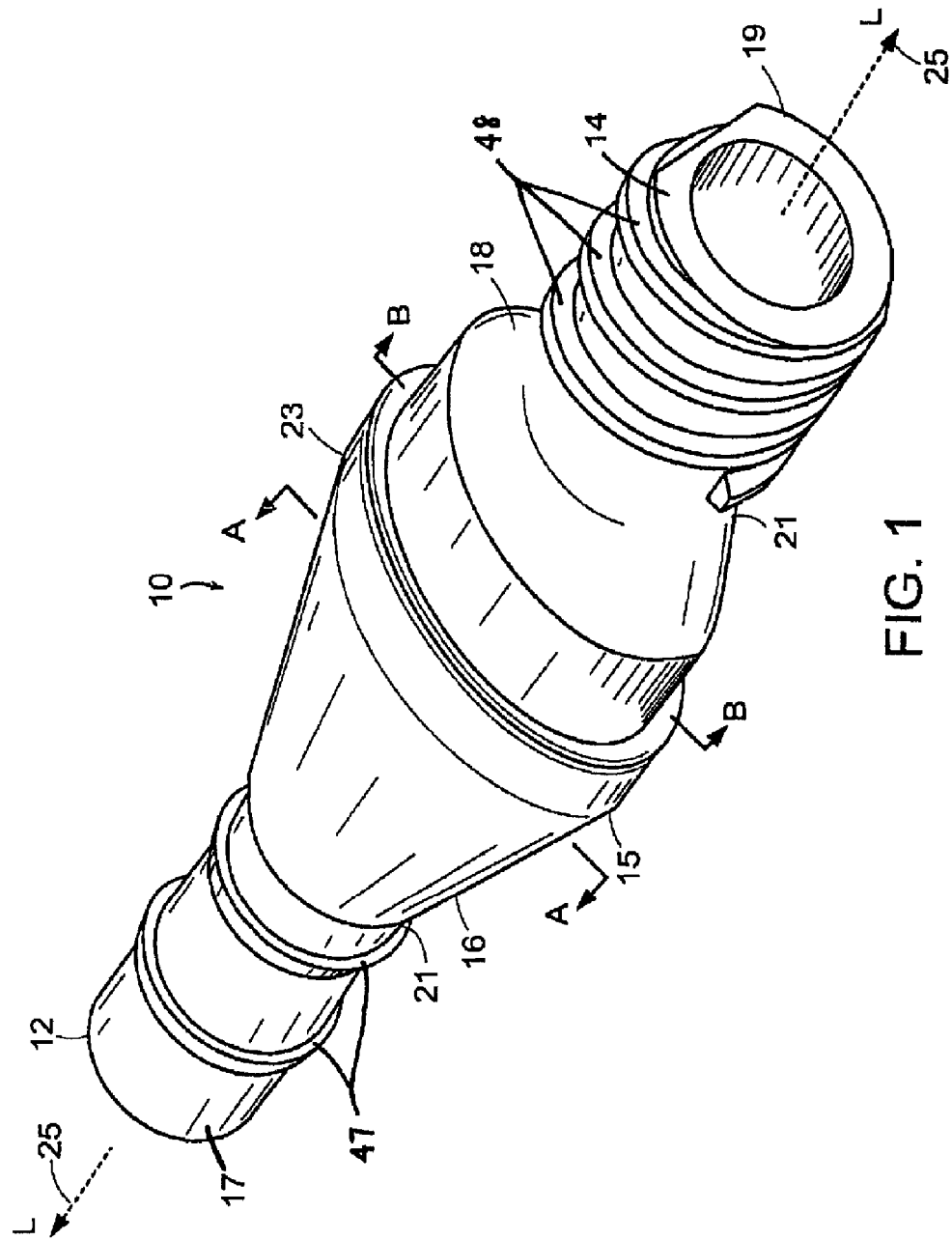
FIG. 1 is schematic view of one embodiment of a pressure activated two-way slit valve assembly according to the invention.

Referring to FIG. 1, a pressure activated two-way slit valve assembly 10 according to the invention includes a first end 12, a second end 14, and a wall 15 extending from the first end 12 to the second end 14. The wall 15 can be made from any relatively rigid, biocompatible, polymer such as, for example, polycarbonate, polyethylene, or ultem® and includes a female housing portion 16 and a male housing portion 18. The male housing portion 18 friction fits within the female housing portion 16, thereby holding the two portions 16, 18 together. In addition to frictional forces, an adhesive can be used to secure a bond between the female and male housing portions 16, 18. Alternatively, the female housing portion 16 can be thermally, chemically, or ionically bonded to the male housing portion 18.

Figure 2:
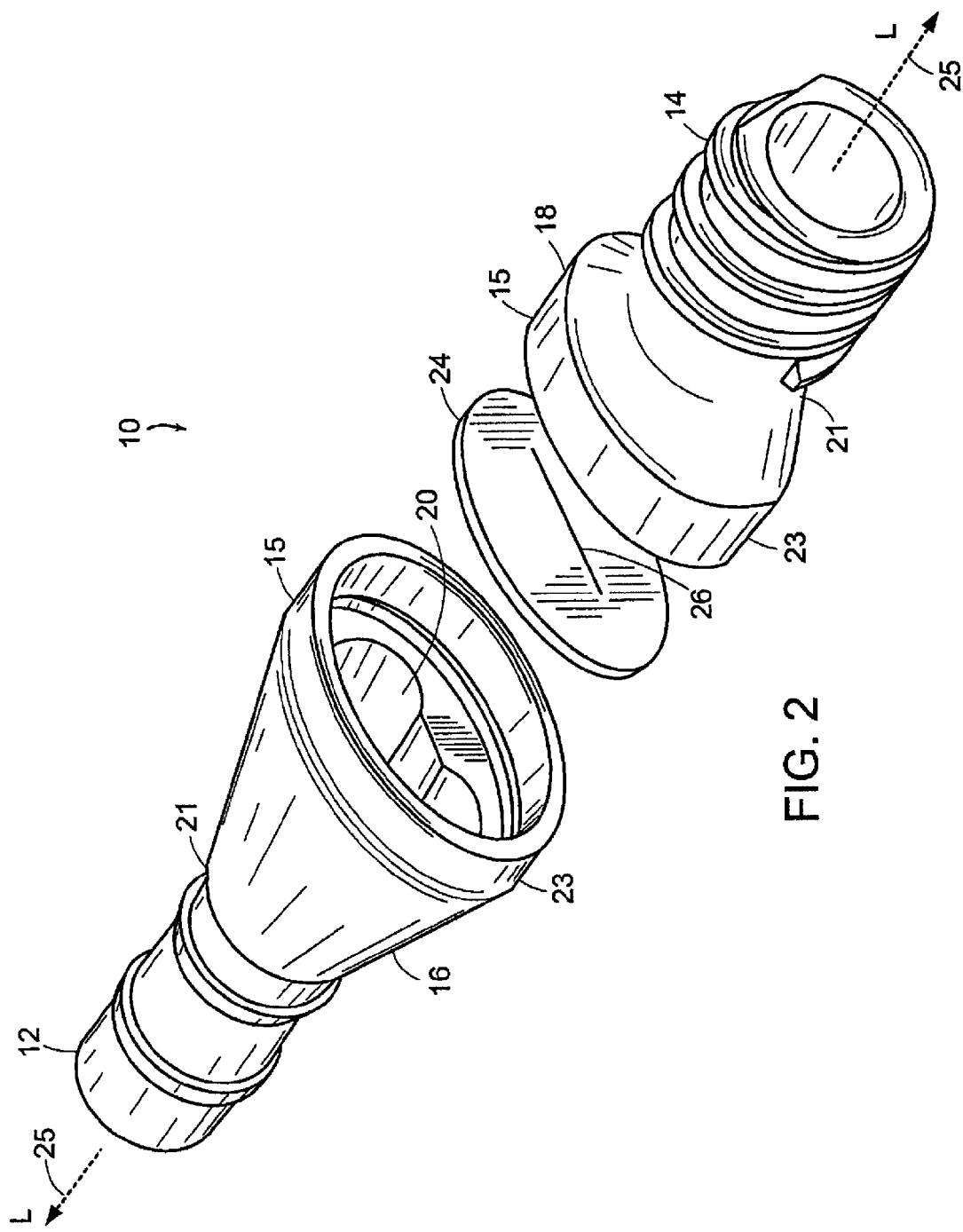
FIG. 2 is an exploded view of the pressure activated two-way slit valve assembly of FIG. 1.

Located at the first and second ends 12, 14 are connection ports 17 and 19 used to interconnect the pressure activated two-way slit valve assembly 10 to other medical devices, such as, for example, catheters, dialysis machines, and end caps. The connection ports 17, 19 can have barbed or luer endings as shown in FIGS. 1 and 2 to aid in attachment between a medical device and the pressure activated two-way slit valve assembly 10. For example, the connection port 17 has barbed endings 47 and the connection port 19 has luer endings 48.

Disposed within the pressure activated two-way slit valve assembly 10 is a flexible, thin disk 24, shown in FIG. 2, that is "sandwiched" between the female housing portion 16 and the male housing portion 18. The flexible, thin disk 24 is preferably made from silicone or other similar flexible polymer and includes a slit 26. The flexible, thin disk 24 is positioned within the pressure activated two-way slit valve assembly 10 such that the slit 26 is perpendicular to line LL, a longitudinal axis 25 of the pressure activated two-way slit valve assembly 10. The slit 26 remains in a closed position as shown in FIG. 2 until a pressure differential having a predetermined force exists within the pressure activated two-way slit valve assembly 10. Once the pressure differential crosses over this predetermined force threshold, the slit 26 separates, thereby allowing blood or fluid to flow therethrough.

Figure 3:
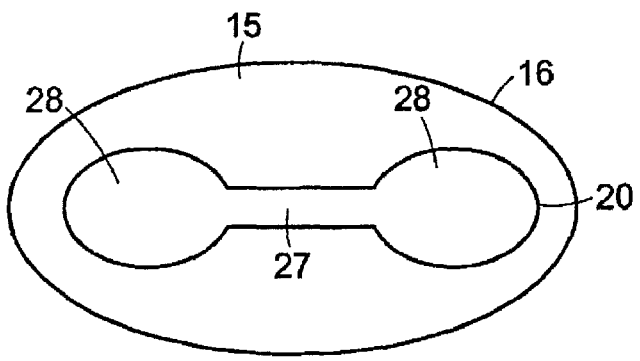
FIG. 3 is a cross-sectional view of a first end portion of the pressure activated two-way slit valve assembly, taken along line AA of FIG. 1.
Figure 4:
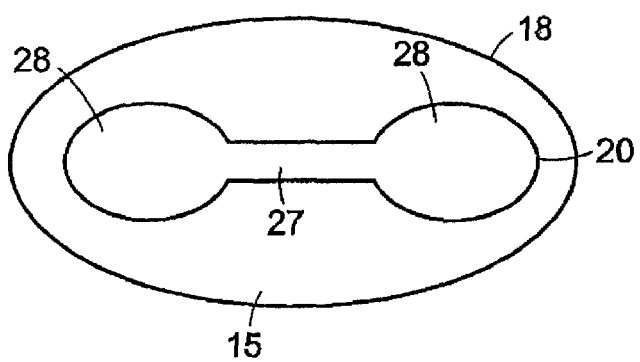
FIG. 4 is a cross-sectional view of a second end portion of the pressure activated two-way slit valve assembly, taken along line BB of FIG. 1.

The pressure activated two-way slit valve assembly 10 also includes a dumbbell shaped channel 20 that is defined by wall 15 and surrounds the flexible, thin disk 24. As shown in FIGS. 3 and 4, the dumbbell shaped channel 20 is disposed within both of the female housing portion 16 and the male housing portion 18. The dumbbell shaped channel 20 has a middle channel portion 27 disposed between and in fluid communication with two large cross-sectional area channel portions 28. The middle portion 27 has a smaller cross-sectional area than the two large cross-sectional area channel portions 28 and thus, restricts the slit 26 from opening prematurely (i.e., under conditions where the pressure differential is below threshold) by decreasing the amount of channel cross-sectional area in a pressure sensitive region. In some embodiments, each large cross-sectional area channel portion 28 has 3 times the cross-sectional area as the middle portion 27. This extra cross-sectional area of the large cross-sectional area channel portions 28 provides the pressure activated two-way slit valve assembly 10 with a large amount of fluid transport area, to maximize fluid flow rates through the pressure activated two-way slit valve assembly 10 once the slit 26 has cracked open. These large cross-sectional area channel portions 28 allow the flow rate through the pressure activated two-way slit valve assembly 10 to maintain a flow rate of up to 500 ml/min. In some embodiments, the large cross-sectional area channel portions 28 allow the flow rate to approach a flow range of about 400 ml/min to 500 ml/min, which is a greater flow rate range than typically achieved in conventional valved high flow rate catheters. An advantage of this greater flow rate range is a decrease in actual catheter use or treatment time. For example, a hemodialysis catheter having a greater flow rate range means that there will be a decrease in dialysis treatment time, which is a greater convenience for both a dialysis patient and for an attending medical professional.

Figure 5:
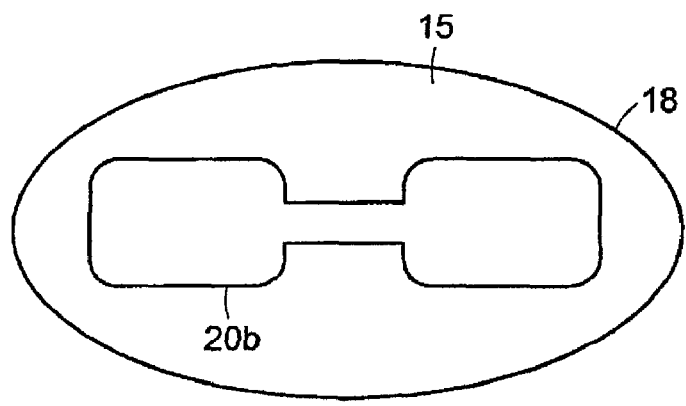
FIG. 5 is a plan-view of an alternative embodiment of a lumen extending through the first and second end portions.
Figure 6:
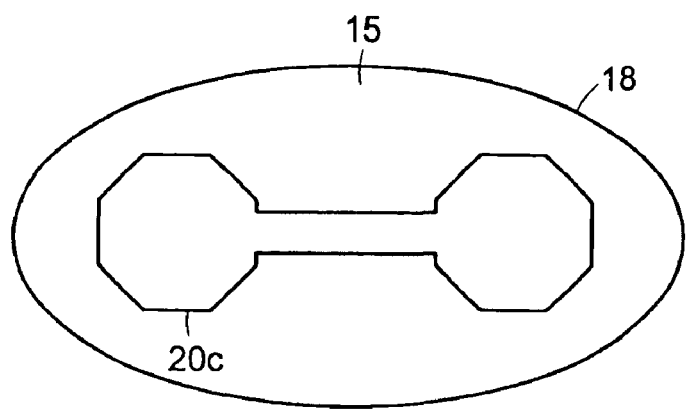
FIG. 6 is another plan-view of another alternative embodiment of a lumen extending through the first and second end portions.

The shape of the dumbbell shaped channel 20 can be slightly modified to produce alternative embodiments of the pressure activated two-way slit valve assembly 10. As depicted in FIGS. 5 and 6, the perimeter of the large cross-sectional area channel portion 28 can be extended to form an elongated dumbbell shaped channel 20b, shown in FIG. 5, or an octagonal dumbbell shaped channel 20c, as shown in FIG. 6. In some embodiments, the size of the middle channel portion 27 is minimized such that the two large cross-sectional area channel portions 28 are separated by a millimeter or less. Other similar embodiments are also possible as long as each large cross-sectional area channel portion 28 has a larger cross-sectional area than the middle portion 27.

Each of the female and male housing portions 16, 18 can taper, as depicted in FIG. 1, from an area of greatest diameter located substantially at connection area 23 to an area of lesser diameter 21. The dumbbell shaped channel 20 disposed within the female and male housing portions 16, 18 tapers along with these portions 16, 18. As the dumbbell shaped channel 20 tapers the shape of the dumbbell shaped channel 20 gradually transforms from a dumbbell structure to an oval or circular structure.

Figure 7:
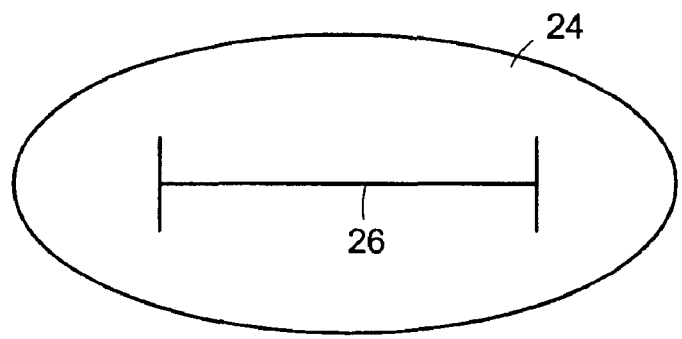
FIG. 7 is a plan-view of a flexible, thin disk that is disposed within the pressure activated two-way slit valve assembly of FIG. 1.
Figure 8:
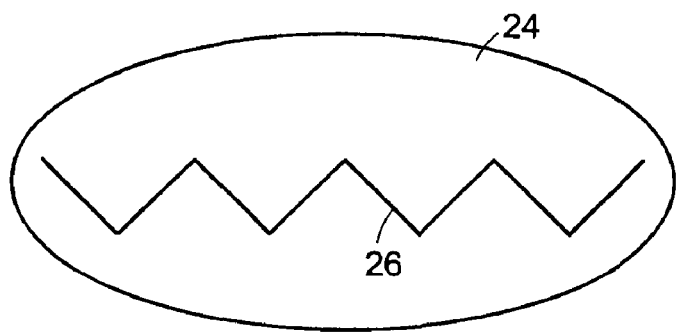
FIG. 8 is a plan-view of another embodiment of a flexible, thin disk.

Located within the dumbbell shaped channel 20, between the female housing portion 16 and the male housing portion 18, is the flexible, thin disk 24 with slit 26. The slit 26 can be a straight slit or, in some embodiments, be H-shaped as shown in FIG. 7. Alternatively, the slit 26 can have a saw-tooth wave shape as shown in FIG. 8. In any case, the size and shape of the slit 26 and the size of the dumbbell shaped channel 20 are designed to enable the slit to deform or crack open when a predetermined pressure differential exists across the pressure activated two-way slit valve assembly 10. Generally, the size of the slit 26 and the dumbbell shaped channel 20 are designed to prevent deformation of the slit 26 until a pressure differential of at least about 50 cm of water exists, thereby minimizing accidental openings of slit 26, which could lead to bleed out or air ingestion. In a preferred embodiment, the dumbbell shaped channel 20 is designed to prevent deformation of the slit 26 until a pressure differential within a range of about 50 cm of water to about 120 cm of water exists. In a more preferred embodiment, the dumbbell shaped channel is designed to prevent deformation of the slit until a pressure differential within a range of about 80 cm of water to about 120 cm of water exists. It is also important to note that the valve may be designed to have the slit crack open at any pressure differential preferred for a particular medical application.

The two-way slit valve assembly 10 allows fluid to flow therethrough in either a proximal direction (i.e., from the first end 12 towards the second end 14) or a distal direction (i.e., from the second end 14 towards the first end 12). As long as the pressure differential across the flexible, thin disk 24 is greater than the threshold, the slit 26 will open automatically and will allow fluids to pass therethrough in either direction.

The particular threshold pressure differential is determined by one or more of the following factors: (1) the thickness of the flexible, thin disk 24, (2) the size of the slit 26, (3) the hardness of the material used to form the flexible, thin disk 24, and (4) the cross-sectional area of the dumbbell shaped channel 20 within each of the female housing portion 16 and the male housing portion 18. For example, the threshold pressure differential value of the two-way slit valve assembly 10 can be customized to a particular value by varying the factors listed above. Thus, if a particular application of the two-way slit valve assembly 10 required a valve, which could open a very low threshold pressure differential value, the material and thickness of the flexible, thin disk 24 and the length of the slit 26 can be selected to accomplish this usage.

In some applications of the two-way slit valve assembly 10, it is important to provide the valve with two different threshold pressure differential values. That is one particular threshold pressure differential value for fluids flowing in the proximal direction and another different threshold pressure differential value for fluids flowing in the distal direction. Embodiments of two-way slit valve assemblies 10 used in these applications can include a dumbbell shaped channel 20 that has a different cross-sectional area dimension in the female housing portion 16 than in the male housing portion 18, so as create two direction sensitive threshold pressure differential values.

The two-way slit valve assembly 10 can be attached to a catheter having a single lumen or alternatively multiple lumens. By way of illustration the following example describes usage of the two-way slit valve assembly in connection with a hemodialysis catheter (a high flow rate catheter) that has two or more lumens.

Referring to FIG. 9, shown is a portion of a hemodialysis catheter 40 attached to two pressure activated two-way slit valve assemblies 10a, 10b according to the invention. The hemodialysis catheter 40 has two distinct lumens 42a, 42b disposed within, as shown in FIG. 10. One of the lumens 42a provides a path for waste-filled blood to exit the patient's body, while the opposing lumen 42b provides a path for blood after dialysis treatment to return to the body. An adapter 34, shown in FIG. 9 and affixed to an end of the hemodialysis catheter 40 further separates these two distinct lumens 42a, 42b into individual tubular elements generally called extension legs 30.

Each extension leg 30 has a single lumen 32 disposed within as shown in FIG. 11. The pair of extension legs 30a, 30b work in combination. One of the extension legs 30a is in fluid connection with the lumen 42a that transports waste-filled blood to a dialysis machine, while the other extension leg 30b is connected to the lumen 42b that carries treated, clean blood back to the patient. Each extension leg 30a, 30b is connected to a pressure activated two-way slit valve assembly 10 that prevents blood from flowing therethrough when dialysis is not in process. The hemodialysis catheter 40 in combination with the extension legs 30a, 30b and pressure-activated slit valve assemblies 10a, 10b can be secured to a patient's body using a wing clip 36 as shown in FIG. 9.

The embodiments shown in FIGS. 9 and 10 depict a hemodialysis catheter 40 having two lumens 42a, 42b. In alternative embodiments, not shown, the hemodialysis catheter 40 or other high flow rate catheter can have more than two lumens. In these embodiments, the additional lumens (i.e., the third, fourth, and so on) can provide access ports for delivery of liquid medicines or other fluids to the patient or for collecting blood specimens from the patient's body. Additional extension legs 30 to connect to the additional lumens 42 would be needed. Each additional extension leg 30 can be outfitted with one pressure activated two-way slit valve assembly 10 if desired.

In some embodiments of this invention, an outer surface 45 of the hemodialysis catheter 40 is coated with an anti-infective coating, such as an antibiotic (for example, tetracycline or doxycycline) or an antimicrobial. These anti-infective coating help prevent the build up of bacteria on the surface of the hemodialysis catheter 40, thereby helping to minimize the possibility of complications caused by infection. The hemodialysis catheter can also have a similar anti-infective coating along a surface 47 of the lumen 42a, 42b. Likewise, the anti-infective coating present along the surface 47 helps to prevent infection within the hemodialysis catheter 40.

Figure 12:
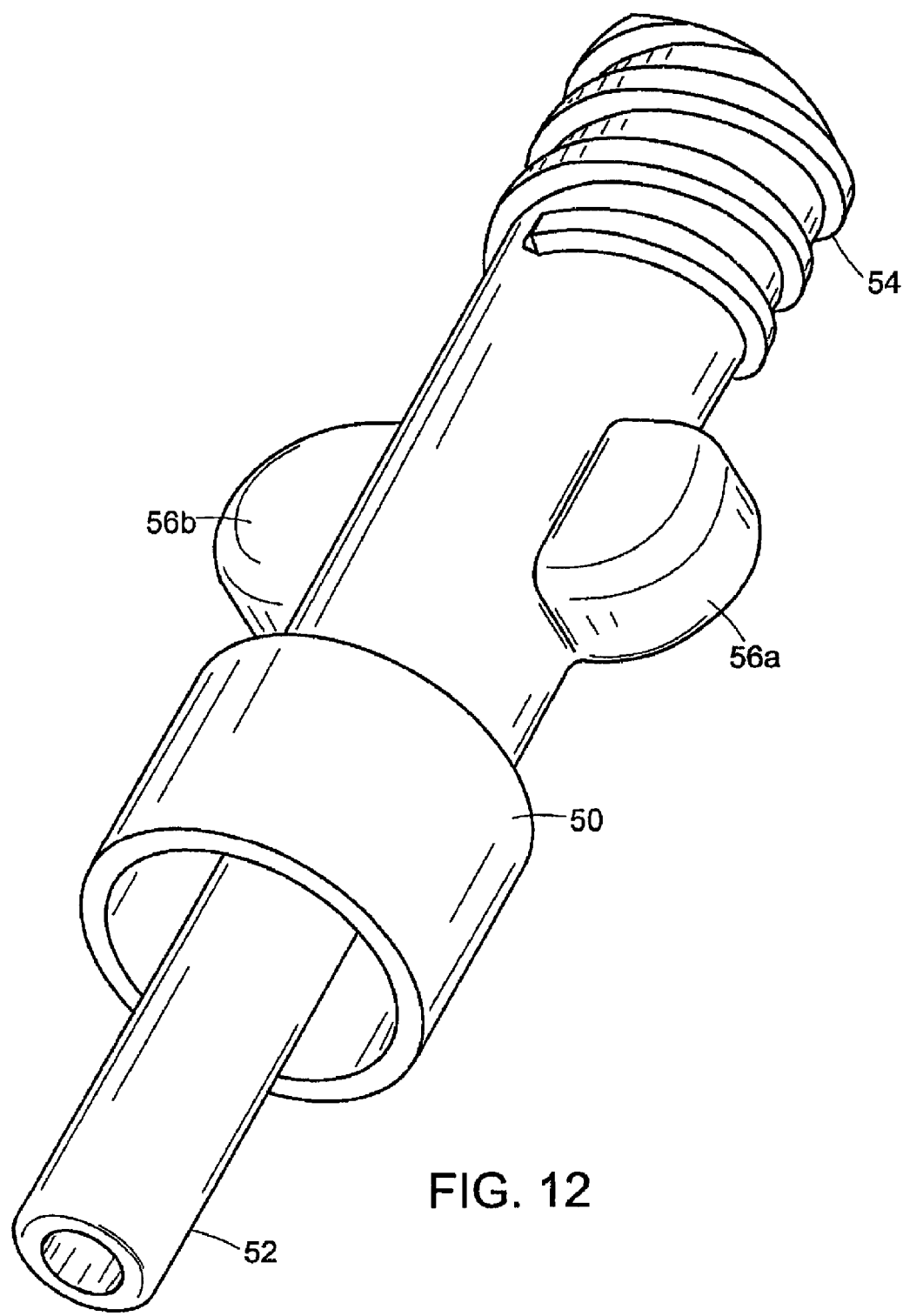
FIG. 12 is a schematic view of an embodiment of a safety, rotatable valve key.
Figure 13:
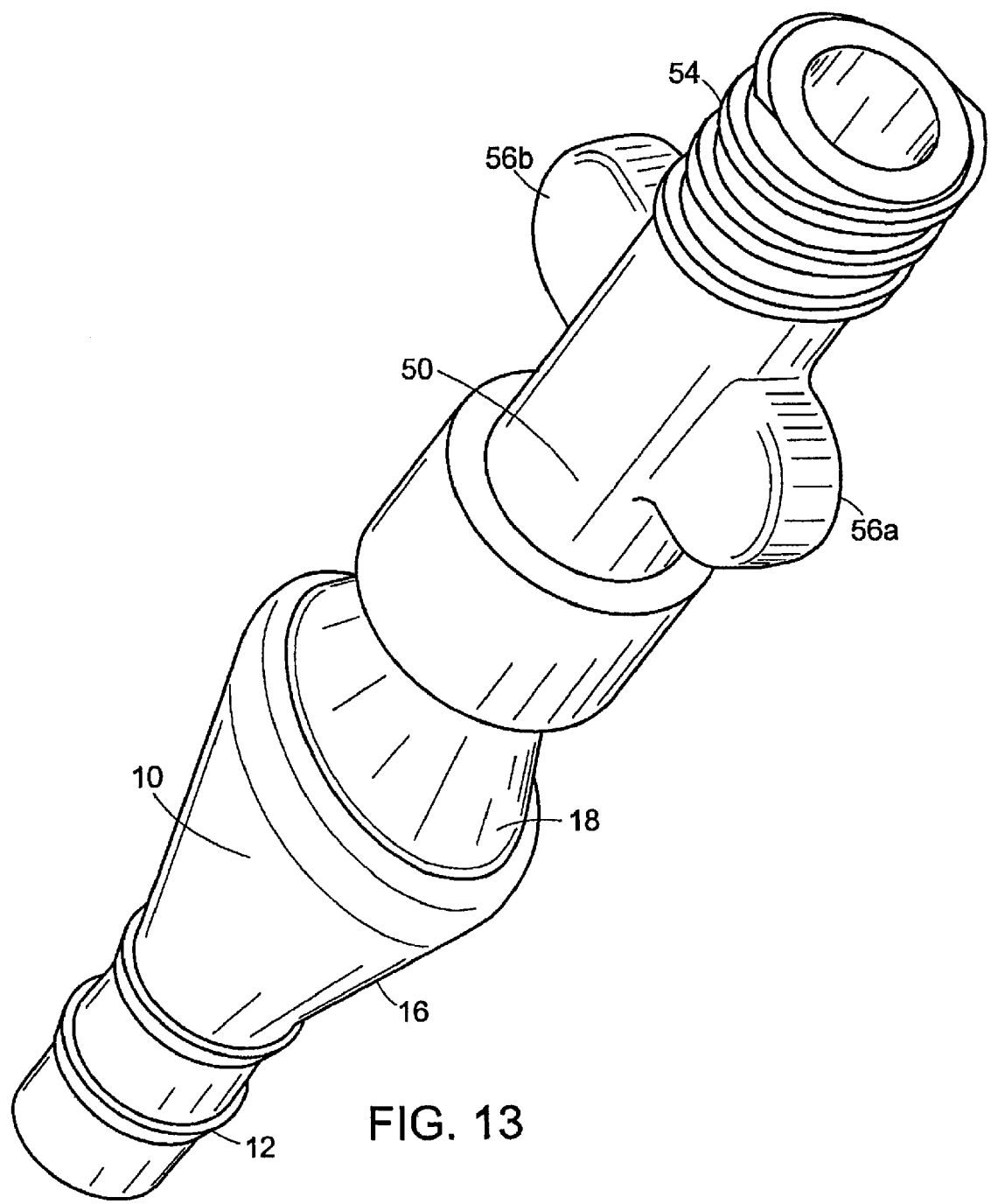
FIG. 13 is a schematic view of the safety, rotatable valve key of FIG. 12 attached to a second end of the pressure activated two-way slit valve assembly of FIG. 1.

An additional feature that can be incorporated into the invention is a safety rotatable valve key 50, an embodiment of which is shown in FIGS. 12 and 13. The safety rotatable valve key 50 can be used force and maintain the slit 26 open to allow for immediate and constant access to the lumens 42 of the hemodialysis catheter 40. The safety rotatable valve key 50 includes an inner tube 52 that can be positioned to extend through the slit 26 when the safety rotatable valve key 50 is rotated from a first position to a second position. The safety rotatable valve key 50 can include a luer ending 54 for attachment to a dialysis machine or an end cap. In addition, the safety rotatable valve key 50 can also include a pair of finger knobs 56a, 56b to aid a medical professional in rotating the safety rotatable valve key 50.

Figure 14:
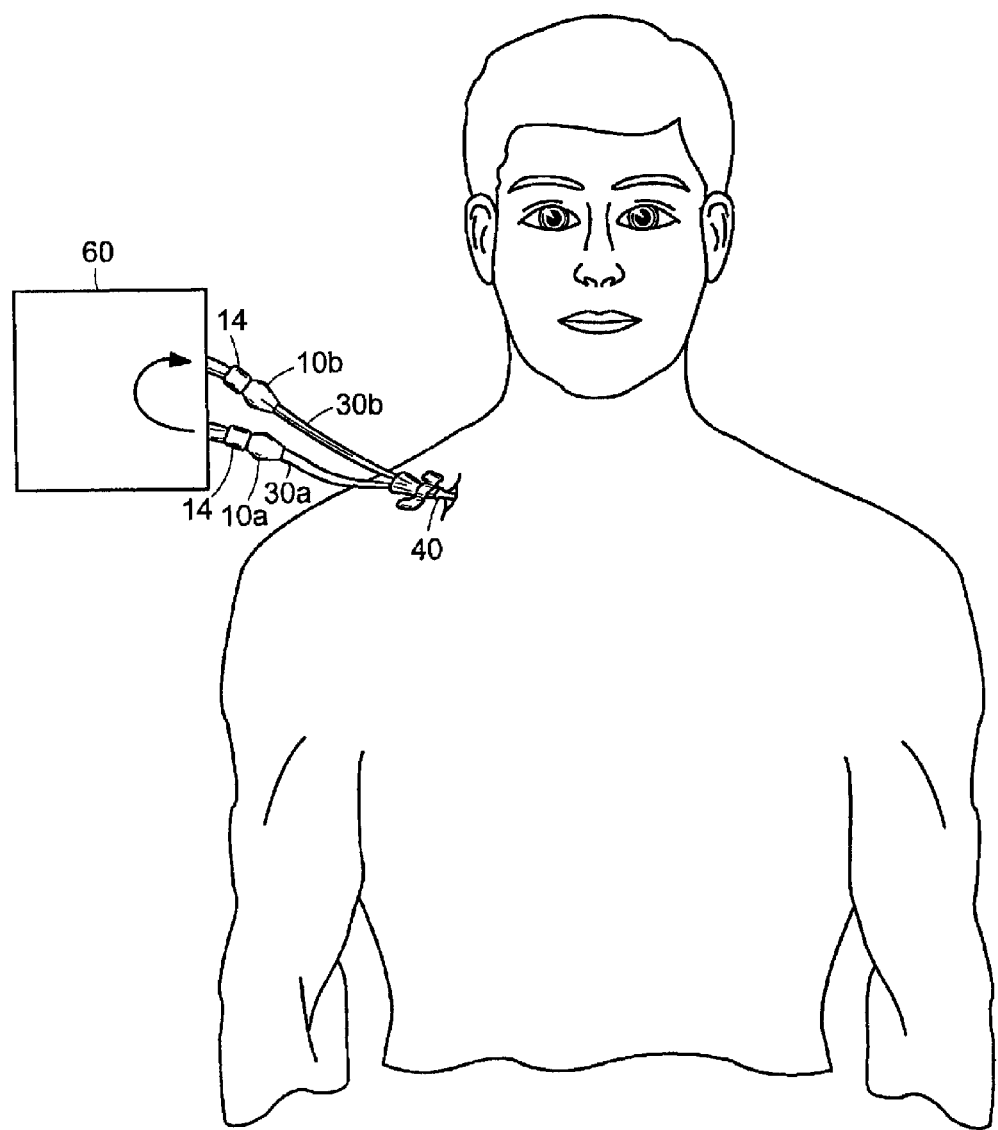
FIG. 14 is a schematic view of a valved dialysis catheter including two pressure activated two-way slit valve assemblies as used during hemodialysis.

In operation, a portion of the hemodialysis catheter 40 is implanted within the patient's body and an open end of the hemodialysis catheter 40 is located within the patient's blood stream. To begin hemodialysis, endcaps are removed from the second end 14 of each pressure activated two-way slit valve assembly 10a, 10b attached to the hemodialysis catheter 40. The second end 14 is then secured to a dialysis machine 60, shown in FIG. 14, that supplies sufficient vacuum force to create the required pressure differential across one the slit 26 of one of the pressure activated two-way slit valve assemblies 10a. Once the slit 26 has cracked open, blood will flow from the patient's body through the hemodialysis catheter 40 to the dialysis machine 60 for treatment (i.e., removal of waste products from the blood). Simultaneously, the dialysis machine 60 forces treated blood through another pressure activated two-way slit valve assembly 10b and into the hemodialysis catheter to be returned to the patient's body.

Variations, modifications, and other implementations of what is described herein will occur to those of ordinary skill in the art without departing from the spirit and scope of the invention. The invention is not to be limited only to the preceding illustrative description.

What is claimed is:

1. A pressure activated two-way slit valve assembly for a catheter, the pressure activated two-way slit valve assembly comprising:

a first end;

a second end;

a wall extending between the first end and the second end, the wall defining a channel having a cross-section located between the first end and the second end, wherein the cross-section includes at least three portions, at least two of the portions being substantially larger than a third portion located therebetween, the cross-section being perpendicular to a longitudinal axis of the of the pressure activated two-way slit valve assembly; and a two-way slit valve disposed within the channel between the first end and the second end, wherein a slit of the slit valve and the channel are sized to enable the slit to deform in response to a predetermined pressure differential across the slit to allow fluid to pass therethrough.

2. The pressure activated two-way slit valve assembly of claim 1, wherein the wall further defines connection ports located at the first end and the second end, the connection ports being in fluid communication with the channel.

3. The pressure activated two-way slit valve assembly of claim 2, wherein the first end comprises a barbed ending for attaching to a catheter.

4. The pressure activated two-way slit valve assembly of claim 2, wherein the second end comprises a luer ending for attaching to one of a dialysis machine and an end cap.

5. The pressure activated two-way slit valve assembly of claim 1, wherein the slit comprises an H-shape.

6. The pressure activated two-way slit valve assembly of claim 1, wherein the slit comprises a saw-tooth wave shape.

7. The pressure activated two-way slit valve assembly of claim 1, further comprising a safety rotatable valve key.

8. The pressure activated two-way slit valve assembly of claim 7, wherein the safety rotatable valve key is attached to the second end.

9. A medical device comprising:
a catheter comprising a distal end, a proximal end, and a housing defining at least one or more lumens extending between the distal end and the proximal end, the distal end being open, and the proximal end including a pressure activated two-way slit valve assembly, the two-way slit valve assembly comprising:
a first end,
a second end,
a wall extending between the first end and the second end, the wall defining a channel having a cross-section located between the first end and the second end, wherein the cross-section includes at least three portions, at least two of the portions being substantially larger than a third portion located therebetween, the cross-section being perpendicular to a longitudinal axis of the of the pressure activated two-way slit valve assembly; and
a two-way slit valve disposed within the channel between the first end and the second end, wherein a slit of the slit valve and the channel are sized to enable the slit to deform in response to a predetermined pressure differential across the slit to allow fluid to pass therethrough.

10. The medical device of claim 9, wherein the wall of the pressure activated two-way slit valve assembly further defines connection ports located at the first end and the second end, the connection ports being in fluid communication with the channel.

11. The medical device of claim 9, wherein the slit of the pressure activated two-way slit valve assembly comprises an H-shape.

12. The medical device of claim 9, wherein the slit of the pressure activated two-way slit valve assembly comprises a saw-tooth wave shape.

13. The medical device of claim 9, wherein the pressure activated two-way slit valve assembly further comprises a safety rotatable valve key.

14. The medical device of claim 13, wherein the safety rotatable valve key is attached to the second end of the pressure activated two-way slit valve assembly.

15. The medical device of claim 1, wherein the housing of the catheter is coated with an anti-infective coating to inhibit bacteria growth.

16. A valved dialysis catheter comprising:
an open-ended multi-lumen catheter including at least one lumen for withdrawing blood form a patient for dialysis and at least one lumen for retuning blood from a dialysis machine to the patient, each lumen of the open-ended multi-lumen catheter including a pressure activated two-way slit valve assembly, each two-way slit valve assembly comprising:
a first end,
a second end,
a wall extending between the first end and the second end, the wall defining a channel having a cross-section located between the first end and the second end, wherein the cross-section includes at least three portions, at least two of the portions being substantially larger than a third portion located therebetween, the cross-section being perpendicular to a longitudinal axis of the of the pressure activated two-way slit valve assembly; and
a two-way slit valve disposed within the channel between the first end and the second end, wherein a slit of the slit valve and the channel are sized to enable the slit to deform in response to a predetermined pressure differential across the slit to allow fluid to pass therethrough.

17. The valved dialysis catheter of claim 16, wherein the wall of the pressure activated two-way slit valve assembly further defines connection ports located at the first end and the second end, the connection ports being in fluid communication with the channel.

18. The valved dialysis catheter of claim 17, wherein the first end of the pressure activated two-way slit valve assembly comprises a barbed ending.

19. The valved dialysis catheter of claim 17, wherein the second end of the pressure activated two-way slit valve assembly comprises a luer ending.

20. The valved dialysis catheter of claim 16, wherein the slit of the pressure activated two-way slit valve assembly comprises an H-shape.

21. The valved dialysis catheter of claim 16, wherein the slit of the pressure activated two-way slit valve assembly comprises a saw-tooth wave shape.

22. The valved dialysis catheter of claim 16, wherein the pressure activated two-way slit valve assembly further comprises a safety rotatable valve key.

23. The valved dialysis catheter of claim 16, wherein the open-ended multi-lumen catheter further comprises an anti-infective external surface.

24. A method for preventing air ingestion in a valved catheter, the method comprising the steps of:
providing a catheter comprising a distal end, a proximal end, and a housing defining at least one or more lumens extending between the distal end and the proximal end, the distal end being open, the proximal end including a pressure activated two-way slit valve assembly comprising:
a first end,
a second end,
a wall extending between the first end and the second end, the wall defining a channel having a cross-section located between the first end and the second end, wherein the cross-section includes at least three portions, at least two of the portions being substantially larger than a third portion located therebetween, the cross-section being perpendicular to a longitudinal axis of the of the pressure activated two-way slit valve assembly, and a two-way slit valve disposed within the channel between the first end and the second end, wherein a slit of the slit valve and the channel are sized to enable the slit to deform in response to a predetermined pressure differential across the slit to allow fluid to pass therethrough; and inserting the distal end of the catheter within a blood vessel.

25. The method of claim 24, wherein the predetermined pressure differential is between about 50 cm of water to about 120 cm of water.

26. The method of claim 24, wherein the predetermined pressure differential is between about 80 cm of water to about 120 cm of water.

27. A pressure activated two-way slit valve assembly for a catheter, the pressure activated two-way slit valve assembly comprising:

a housing including a channel, wherein:
- a cross-section of the channel is perpendicular to a longitudinal axis of the housing, and
- at least two portions of the cross-section are substantially larger than a third portion of the cross-section located therebetween; and a two-way slit valve disposed within the channel, wherein a slit of the slit valve is longitudinally aligned with the third portion.

* * * * *